(12) United States Patent
Bayoudh et al.

(10) Patent No.: US 7,910,383 B2
(45) Date of Patent: Mar. 22, 2011

(54) MOLECULAR FINGERPRINTS WITH ENHANCED IDENTIFYING CAPABILITY, METHOD FOR PREPARING SAME AND USE THEREOF

(75) Inventors: Sami Bayoudh, Mont Saint Aignan (FR); Kaynoush Naraghi, Mont Saint Aignan (FR); Michel Arotcarena, Rouen (FR)

(73) Assignee: Polyintell, Rouen (FR)

( * ) Notice: Subject to any disclaimer, the term of this patent is extended or adjusted under 35 U.S.C. 154(b) by 98 days.

(21) Appl. No.: 11/988,050

(22) PCT Filed: Jul. 4, 2006

(86) PCT No.: PCT/IB2006/052250
§ 371 (c)(1),
(2), (4) Date: Apr. 2, 2008

(87) PCT Pub. No.: WO2007/004197
PCT Pub. Date: Jan. 11, 2007

(65) Prior Publication Data
US 2009/0123411 A1   May 14, 2009

(30) Foreign Application Priority Data
Jul. 4, 2005   (FR) .................................. 05 52032

(51) Int. Cl.
*C08J 9/26* (2006.01)
*C08J 9/28* (2006.01)
*G01N 33/543* (2006.01)
*G01N 33/545* (2006.01)
*G01N 33/551* (2006.01)

(52) U.S. Cl. .......... 436/518; 436/524; 436/531; 521/61; 521/63

(58) Field of Classification Search ........................ None
See application file for complete search history.

(56) References Cited

U.S. PATENT DOCUMENTS

| | | | |
|---|---|---|---|
| 4,127,730 A | 11/1978 | Wulff et al. | |
| 4,208,356 A * | 6/1980 | Fukawa et al. ................. | 525/89 |
| 5,110,833 A | 5/1992 | Mosbach | |
| 6,458,599 B1 * | 10/2002 | Huang ........................... | 436/518 |
| 6,582,971 B1 * | 6/2003 | Singh et al. ................... | 436/518 |
| 6,660,176 B2 * | 12/2003 | Tepper et al. .................. | 216/56 |
| 6,852,818 B1 * | 2/2005 | Piletsky et al. .............. | 526/303.1 |
| 2003/0165987 A1 | 9/2003 | Huang | |
| 2003/0186328 A1 * | 10/2003 | Carter et al. ................... | 435/7.1 |

FOREIGN PATENT DOCUMENTS

| | | |
|---|---|---|
| WO | WO 95/21673 A1 | 8/1995 |
| WO | WO 01/32760 A1 | 5/2001 |
| WO | WO 01/61354 A1 | 8/2001 |
| WO | WO 01/61355 A1 | 8/2001 |
| WO | WO 01/90228 A1 | 11/2001 |
| WO | WO 2004/067578 A1 | 8/2004 |

OTHER PUBLICATIONS

Whitcombe, M., et al. "A New Method for the Introduction of Recognition Site Functionality Into Polymers Prepared by Molecular Imprinting: Synthesis and Characterization of Polymeric Receptors Cholesterol." *J. Am. Chem. Soc.*, vol. 117, pp. 7105-7111 (1995).
Striegler, S., et al. "Evaluation of New Strategies to Prepare Templated Polymers with Sufficient Oligosaccharide Recognition Capacity." *Analytica Chimica Acta*, vol. 284, pp. 53-62 (2003).
Cormack, P., et al. "Molecularly Imprinted Polymers: Synthesis and Characterisation." *Journal of Chromatography B*, vol. 804, pp. 173-182 (2004).
Olwill, A., et al. "The Use of Molecularly Imprinted Sol-Gels in Pharmaceutical Separations." *Biosensors and Bioelectronics*, vol. 20, pp. 1045-1050 (2004).
Blomgren, A., et al. "Extraction of Clenbuterol from Calf Urine Using a Molecular Imprinted Polymer Followed by Quantitation by High-performance Liquid Chromatography with UV Detection." *Journal of Chromatography*, vol. 975, pp. 157-164 (2002).
Anderson, L., et al. "A Highly Selective Solid Phase Extraction Sorbent for Pre-Concentration of Sameridine Made by Molecular Imprinting." *Chromatographia*, vol. 46, No. 1/2, pp. 57-62 1997).
Crescenzi, C., et al. "Determination of Clenbuterol in Bovine Liver by Combining Matrix Solid-Phase Dispersion and Molecularly Imprinted Solid-Phase Extraction Followed by Liquid Chromatography/Electrospray Ion Trap Multi-Stage Mass Spectometry." *Anal. Chem.*, vol. 73, pp. 2171-2177 (2001).
Zhang, G., et al. "Interpolymer Complexes Comprising Block Copolymers Due to Specific Interactions." *Materials Science and Engineering C*, vol. 10, pp. 155-158 (1999).
Makote, R., et al. "Template Recognition in Inorganic-Organic Hybrid Films Prepared by the Sol-Gel Process." *Chem. Matter*, vol. 10, pp. 2440-2445 (1998).
Zhang, G., et al. "Intermacromolecular Complexation Because of Specific Interactions 11. Ionic Interaction Complexation and its Comparison With Hydrogen-Bonding Complexation." *Polymer*, vol. 42, pp. 151-159 (2001).
Chapuis, F., et al. "Optimization of the Class-Selective Extraction of Triazines From Aqueous Samples Using a Molecularly Imprinted Polymer by a Comprehensive Approach of the Retention Mechanism." *Journal of Chromatography A*, vol. 999, pp. 23-33 (2003).

* cited by examiner

*Primary Examiner* — Mark L Shibuya
*Assistant Examiner* — Leon Y. Lum
(74) *Attorney, Agent, or Firm* — Oliff & Berridge, PLC

(57) ABSTRACT

The invention concerns a method for preparing a molecular fingerprint comprising sites for identifying at least one target molecule, the fingerprint being obtained from at least one master molecule of polymeric type, called master polymer. The invention is characterized in that the master polymer is different from the target molecule(s), and is capable of being eliminated by degradation and/or washing, and that at least 5% in number of monomer units constituting the master polymer are involved in the formation of the sites for identifying the target molecule(s).

24 Claims, No Drawings

MOLECULAR FINGERPRINTS WITH ENHANCED IDENTIFYING CAPABILITY, METHOD FOR PREPARING SAME AND USE THEREOF

The present invention relates to the field of molecular fingerprints prepared from masters, useful for identifying target molecules.

The present invention aims in particular at a new method for preparing molecular fingerprints from molecules of polymeric type, called master polymers, notably having an improved identification capacity with regards to target molecules having only one part of the constitutive patterns of the master molecules, as well as an improved stabilization of the complex formed by the fingerprint and the master molecules.

The present invention also relates to the molecular fingerprints likely to be obtained by this method, along with their use.

The materials with molecular fingerprints, still called MIPs in the English language, are obtained by a molecular imprinting technique.

Generally, these molecular fingerprints are obtained by copolymerizing monomers and crosslinking agents in the presence of a molecule which one precisely seeks to attach the fingerprint. The monomers are arranged specifically around this master molecule by strong or weak interactions, then are generally polymerized with a high crosslinking agent content. After polymerization, the molecule is extracted from the polymer material and thereby leaves its molecular fingerprint, thus cavities within the material. These cavities are real synthetic receptors comparable with the biological receptors of the antibody type. These artificial antibodies, materials with molecular fingerprints, were used in the applications of chromatography separation, the sensors, the catalysis of chemical reaction, the solid-phase extraction, the immunoanalysis, the molecular library screening.

There are two possible approaches to make molecular fingerprints: the covalent approach developed by Wulff in U.S. Pat. No. 4,127,73, and the non-covalent approach developed by Mosbach in U.S. Pat. No. 5,110,833.

In the covalent approach, the interactions between the monomers and the master molecule are of labile covalent bonds type. In this case, after the extraction of the master molecule by rupture of the covalent bond, the identification is also carried out by the formation of a covalent bond between the fingerprint and the target molecule.

In the non-covalent approach of Mosbach, the interactions between the monomers and the target molecule are weak bonds of hydrogen bonds, ionic bonds, pi donor-pi acceptor, Van Der Waals bonds and hydrophobic interactions type. After the extraction of the master molecule, the identification is also carried out by non-covalent interactions between the fingerprint and the target molecule.

The two approaches can be combined using the first approach of covalent type for preparing the material with molecular fingerprint, and to obtain an identification by non-covalent interactions, as disclosed by M. J. WHITCOMBE et al. in "A New Method for the Introduction of Recognition Site Functionality into Polymers prepared by molecular Imprinting: Synthesis and Characterization of Polymeric Receptors for Cholesterol" *J. Am. Chem. Soc.*, 1995, 117, 7105-7111.

All the above-mentioned approaches generally use a "master molecule", identical or analogous to the target molecule to be identified, in particular having a similar molecular size.

This imprinting technique showed its effectiveness when the imprinting was carried out in aprotic organic solvents but, on the other hand, showed weaknesses and limitations when the imprinting was carried out in polar protic solvents (water, alcohols). We are then confronted with a stabilization failure of the complex between the monomers and the master molecule, which rests primarily on hydrogen, ionic and Van Der Waals bonds in the most traditional cases.

Attempts were made to promote the identification in water or in polar protic solvents, notably of sugars by implementing interactions of the metallic coordination type (Striegler et al. "Evaluation of new strategies to prepares templated polymers with sufficient oligosaccharide recognition capacity", Analytica Chimica Acta 484, 2003, 53-62) without however, giving entire satisfaction.

Also for the development of fingerprints useful for an identification in water, very hydrophilic matrixes were prepared for the riboflavine and its derivatives in WO 2004/067578.

Another disadvantage of the use of molecular fingerprints prepared from master molecules having substantially the same molecular size, lies in the difficulty of ensuring a total extraction of the master molecules at the end of the realization of the fingerprint. Thereby, one cannot completely free oneself from the risk that these residual master molecules are salted out during the use of the fingerprints for detection of these same molecules, leading then to wrong positives.

A solution was brought to this problem, consisting in using a chosen analogue so as to be able to distinguish it during analysis. However, the analogue also being salted out and the analysis not always making it possible to entirely distinguish the analogue from the target, the method presents some disadvantages. Examples of this method can be found in A. Blomgren et al. "Extraction of Clenbuterol from calf urine using a molecularly imprinted polymer followed by quantitation by high-performance liquid chromatography with UV detection", *Journal of Chromatography* A, 975 (2002), 157-164, where the clenbuterol is the target and the brombuterol, namely the analogue, is the master. We can also mention the two following articles: L. I. Anderson et al. "A Highly Selective Solid Phase Extraction Sorbent for the Concentration of Sameridine Made by Molecular Imprinting", *Chromatographia* 46 (1997) 57-62, C. Crescenzi et al., "Determination of Clenbuterol in bovine liver by Combining Matrix Solid-phase dispersion and Molecularly Imprinted Solid-phase extraction followed by Liquid Chromatography/Electrospray ion trap multiple stage Mass Spectrometry", *Anal. Chem.* 73 (2001) 2171, 1986.

Other methods for preparing molecular fingerprints have been developed.

The "epitope" approach, developed for the sake of identification of macromolecules, is notably described in patent applications WO 01/61355 and WO 01/61354. In this method, contrary to the traditional approaches, the master molecule has a molecular size lower than that of the target molecule. Typically, a peptide moiety is used as master for the identification by the molecular fingerprint of a protein.

Still according to another method, disclosed in particular in patent application WO 01/32760, the master molecule or one of its analogues is grafted on a solid porous silica support before proceeding to the polymerization to obtain the molecular fingerprint inside the support. Thereby, we carry out the extraction of the support and the molecule. The use of such a support for the grafting of master molecules was also disclosed in WO 95/21673, with an agarose support for example, as well as in WO 01/90228. In this last document, the nature of the support was generalized. This last technique allows molecular fingerprints to be formed, whose sites for identifying are located as close as possible to the polymer surface and/or polymer pores, and essentially meets a need to provide molecular fingerprints comprising homogeneous sites for identifying, steered in an uniform way, no longer requiring pore forming solvents and improving the accessibility of the sites. However, the use of this type of fingerprint can cause compatibility problems between the fingerprint itself and the manufacturing solvent, namely the solvent in which the polymerization of the fingerprint is performed. In other words, it is not always possible to find suitable support, particularly in terms of wettability, for a given type of solvent.

There is therefore a need to jointly optimize both the handling ability of these molecular fingerprints, as well in their preparation as in their use in protic and polar solvents, and notably aqueous, and their identification capacity.

Moreover, a need exists to have molecular fingerprints whose non-desired salting-out of master molecules is not likely to distort the performance of the molecular fingerprint during its use.

Further, a need exists to improve the stabilization properties of the complex in balance formed by the master molecule and the matrix of the molecular fingerprint, in particular in the protic solvents.

Moreover, a need exists to have molecular fingerprints whose master molecules can be easily recycled.

Further, a need exists to have molecular fingerprints whose master molecules can be easily recovered, notably in the case of toxic molecules.

Finally, a need exists to obtain molecular fingerprints having an improved identification capacity, namely very dense in sites for identifying and/or provided with a good accessibility for the target molecules.

The object of the present invention is more precisely a method for preparing a molecular fingerprint comprising sites for identifying at least one target molecule, said fingerprint being obtained from at least one master molecule of polymeric type, called master polymer, characterized in that said master polymer is different from the target molecule(s), and is capable of being eliminated by degradation and/or washing, and that at least 5% in number of monomer units constituting said master polymer are involved in the formation of the sites for identifying the target molecule(s).

Still according to another of its aspects, the present invention relates to a method for preparing a molecular fingerprint intended for identifying at least one target molecule, characterized in that it comprises at least:
  a monomer polymerization step intended to form the matrix of the molecular fingerprint in the presence of a master polymer as previously defined, and
  a master polymer elimination step by degradation and/or washing.

According to still another aspect, the invention relates to the molecular fingerprint liable to be obtained by the method according to the present invention.

Finally, according to a last aspect, the object of the present invention is the use of the molecular fingerprint obtained according to the method of the present invention for extraction, detection, separation, purification, absorption, adsorption, retention or controlled release, or even in applications chosen from the sensors, the catalysis, the screening of molecules, the directed chemical synthesis, the treatment of sample, the combinatory chemistry, the chiral separation, the group shielding, the balance movement, the polymer drugs or even the encapsulation.

Thereby, the inventors were able to note that the fingerprint prepared according to the method, which is an object of the present invention, enables to stabilize the complex in balance between the master polymer and the molecular fingerprint in formation. This stabilization enables identifying effects to be obtained, higher than the existing state of the art, and enables the stabilization of the complex in polar and protic mediums such as water, alcohols etc. The identification in these mediums is thus more effective.

This type of interpolymer interaction was studied in particular by G. Zhang et al., in "Interpolymer complexes comprising block copolymers due to specific interactions", *Materials Science and Engineering C* 10 (1990) 155-158, and by G. Zhang et al., "Intermacromolecular Complexation because of Specific Interactions 11. Ionic Interaction Complexation and its Comparison with Hydrogen-bonding Complexation", *Polymer* 42 (2001) 151-159.

The fingerprints prepared according to the method subject-matter of the present invention, further advantageously contain areas with a high density of sites for identifying in the material, thanks to the good affinity between the polymeric material constituting the fingerprint matrix and the master polymer. This good affinity favors the internalization of a greater number of master polymers, and thus finally leads to fingerprints provided with a significant and enhanced identification capacity.

By "significant and enhanced identification capacity", we mean for example, within the scope of this invention, that the identification capacity of the fingerprint formed from a master polymer is increased by at least 15%, compared to the identification capacity of a fingerprint formed from the same matrix but with, as master molecule, a non-polymeric molecule, namely the target molecule or one of its analogues, in similar preparation conditions. This improvement is notably illustrated in examples 4 and 8 in relation to the identification of naphthol and BOC-(L)-Tyrosin, respectively.

Furthermore, the invention has the advantage of solving the problem due to the salting-out of master molecules that distort the performance of the fingerprint when the master molecule is identical or an analogue of the target molecule. Thereby, according to this invention, the target molecule not being the master, which is a polymer, the measurements of trace analysis are not distorted by this release.

The invention also enables the porosity of the material to be increased, and thus facilitates the access of the target molecules and enables, if necessary, to not use pore forming solvent.

The sites for identifying the fingerprints prepared according to the method subject-matter of the present invention, further have the advantage of being homogeneous, in that they have close sizes and configurations. Their accessibility by a target molecule, as well as the identification step of said target molecule are therefore similar, for all of the sites of identification, which can for example result in a lower mid-height width of the chromatographic peaks reporting the retention times of said target molecules in a chromatographic column filled with a fingerprint according to the invention, with respect to a column filled with a fingerprint of the prior art.

This greater homogeneity of the sites for identifying, but also of their accessibility is illustrated in particular by HPLC measurements which appear in example 7.

According to the present invention,
  "target molecule" means, any entity able to bind specifically to the molecular fingerprint,
  "master polymer" means, the polymer used according to the present invention as master for preparing the molecular fingerprint,
  "pattern of the monomer unit useful for the formation of the site for identifying" means, a part of said monomer unit which is involved in the formation of the site for identifying, "moiety of target molecule useful for the identification" means, the part of the target molecule which is involved in the identification when using the molecular fingerprint, "site for identifying" means, the cavity of the matrix of the molecular fingerprint which indeed is involved in the identification of the target molecule(s), "identification capacity" means, the quantity of target molecules being able to be identified with respect to the total quantity of the molecular fingerprint, the quantity being expressed in the same unit. It can be measured advantageously in mass of target molecules identified by mass of the molecular fingerprint.

Within the scope of the present invention, the molecular fingerprint according to the invention, can be intended to identify several target molecules according to the desired use. Thereby, unless otherwise specified, the invention is not limited to the single embodiment in which the identification properties aim only one target molecule.

According to the present invention, "polymer" means a product consisted of a set of macromolecules obtained after the polymerization or copolymerization of monomers, and characterized by certain properties such as the molecular mass. Thereby, for example, an homopolymer comprises only one kind of monomer units, but can comprise macromolecules having different molecular masses.

According to the present invention, "monomer" covers a molecule able to be converted into a polymer by combination with itself or with other molecules of the same type.

According to the present invention, "copolymer" means a polymer derived from at least two types of monomers.

Moreover, according to the present invention:

"monomer unit" means the largest constitutive unit of the macromolecule structure formed from only one monomer molecule, "constitutive unit" means an atom or a group of atoms, including the atoms or groups of atoms possibly attached, which constitute a fundamental part of the macromolecule structure, "block" means a part of a macromolecule comprising many constitutive units, and which has at least a constitution or configuration particularity which does not appear in the adjacent portions, "polymer chain" or "chain" means a macromolecule, or a part thereof, comprising a linear or branched sequence of subsequent units located between two subsequent limit units which can each be an end group, a branch point or a particularity feature of the macromolecule, "polymer with blocks" and "copolymer with blocks" respectively mean a polymer whose macromolecules consist of linearly linked blocks, and a polymer with blocks derived from several species of monomers. They can be regular, irregular or block polymers, "graft polymer" and "graft copolymer" mean a polymer made up of macromolecules comprising blocks linked to the main chain; these blocks constitute side chains, and present constitution or conformation features different from those of the main chain, and respectively a graft polymer derived from several species of monomers, "comb-shaped polymer" or "comb-shaped copolymer", which is a sub-category of graft polymers or copolymers, means a polymer or copolymer presenting a linear skeleton of a certain chemical type and polymer chains called "side branches", of an identical or different chemical type, also linear but significantly shorter than the skeleton, attached covalently to said skeleton by one of their ends, "alternating copolymer" means a copolymer consisting of macromolecules comprising two kinds of monomer units, distributed alternately, "statistical copolymer" means a copolymer consisting of macromolecules in which the distribution of the monomer units obeys known statistical laws, and "random copolymer" means a copolymer consisting of macromolecules in which the probability of finding a given monomer unit at a given point of the chain is independent from the type of the adjacent units, "copolymer with gradient", which is a sub-category of the statistical copolymers, indicates copolymers having an evolution of the ratio of the various monomers throughout the chain. The distribution in the polymeric chains of the comonomers depends on the evolution during the synthesis of the relative contents of the comonomers, "block copolymer" means a copolymer whose constitutive units follow one another in a defined order, "hyperbranched polymer" means the polymers having a tree structure, "dendrimer" characterizes a three-dimensional structure. The dendrimers are related with hyperbranched polymers, in which the branched monomers are associated according to a tree process around a multivalent central core.

In the case of a branch which comprises a single fixation point, we deal with a "star-shaped polymer".

"comprised between . . . and . . . " means that the terminals are also described.

Master Polymer: Homopolymer or Copolymer

According to the present invention, the molecular fingerprints are formed, during their preparation method, around the macromolecules constituting the master polymer. The method can implement several types of master polymers simultaneously.

The fingerprint thereby obtained is then used for its identifying properties with respect to constitutive patterns of the macromolecules, and not of the macromolecules themselves.

According to the present invention, at least 5% in number of monomer units constituting the master polymer are involved in the formation of the sites for identifying the target molecule(s). Advantageously, the monomer units being involved in the formation of the sites for identifying the target molecule(s) constitute together or separately at least one moiety of the target molecule(s).

More precisely, according to one preferred embodiment of the present invention, the master polymer contains at least 5% of monomer units comprising at least one pattern useful for the formation of the sites for identifying the target molecule(s).

When the molecular fingerprint is able to identify only one target molecule, several cases can arise, which are all part of the invention.

In a first case, at least 5% in number of monomer units comprise each one at least one pattern useful for the formation of a site for identifying, each one corresponding to the target molecule as such.

In a second case, at least 5% in number of monomer units comprise at least one pattern useful for the formation of a site for identifying corresponding to one moiety of the target molecule. In other words, only one part of the target molecule is retained in the site for identifying.

In a third case, it is the whole monomer unit which corresponds to the target molecule as such. Therefore, at least 5% in number of monomer units are each one useful for the formation of a site for identifying, each one corresponding to the target molecule.

In a fourth case, it is the whole monomer unit which corresponds to one moiety of the target molecule. Thus, at least 5% in number of monomer units are each one useful for the formation of a site for identifying, each one corresponding to one moiety of the target molecule.

We specify that the term "corresponds" was used to include the case where there is not total identity, namely where minor substitutions lead to chemical analogues which do not affect the identification step.

To illustrate the use of master molecules slightly different from the target molecules which can be called "analogues", we can notably mention F. Chapuis et al. "Optimization of the Class-selective Extraction of Triazines from Aqueous Samples using a Molecular by Imprinted Polymer by a Comprehensive Approach of the Retention Mechanism", *Journal of Chromatography A*, 999 (2003) 23-33, in which the terbutylazine is used as master molecule enabling the identification of a certain number of compounds of the same triazine family. In the same way, the bromoclenbuterol can be used as master molecule, for the analysis of the clenbuterol (see in particular above-mentioned publications Blomgren et al. and C. Crescenzi et al.), or even an analogue of the sameridine to detect the sameridine (see above-mentioned publication L. I. Anderson et al.).

Moreover, we note that, as will be more detailed in the following description, the molecular fingerprint according to the present invention can be able to identify several target molecules insofar as the master polymer contains the adequate monomer units, namely being involved in the formation of the sites for identifying said target molecules. The above-mentioned cases, when the target molecule is single, also apply in the event of a plurality of target molecules.

Considering the aforementioned, the present invention notably relates to a method for preparing one molecular fingerprint as defined above, further characterized in that at least 5% in number of the monomer units each constitute or comprise at least one target molecule, or one of its moieties useful for the identification.

Typically in the above-mentioned case, in which only one pattern of the monomer unit is involved in the formation of the site for identifying, this pattern can be bound in the monomer unit to the polymerizable chain by an adapted linker, and thereby constitute one part of the side chain of the master polymer.

Always in this case, but according to another alternative, the target molecule can also be a dimer from which are derived two close monomer units, a trimer, or even one of their chemically close analogues. We therefore specify, both, even the three monomer units intended for the formation of the site for identifying the target molecule are comprised in the 5% defined above. Thereby, the invention also relates to a method for preparing one molecular fingerprint as defined above, further characterized in that at least two, three, even several monomer units, identical or different and subsequent reproduce together at least a target molecule, or one of its moieties useful for the identification.

In the case of multiple target molecules, from two to four target molecules for example, the 5% defined above comprise the total number of the monomer units intended for the formation of the sites for identifying the target molecules.

It is specified that according to the specific case, and particularly according to the configuration of the master polymer, the fingerprint will be more or less selective with respect to the identification of a mixture of molecules, related to a monomer and/or a dimer and/or a trimer.

According to a preferred embodiment, the ratio between the molecular mass of the master polymer or the average molecular mass of all of the master polymers and the molecular mass of the target molecule or the average molecular mass of all of the target molecules is comprised between 500 and 50,000. By way of illustration, for non-degradable polymers, this ratio can vary preferably between 500 and 2000, and for degradable polymers, this ratio can advantageously vary between 500 and 10,000.

The master polymer must be removable. The removal can be carried out by degradation and/or washing. Thus, the largest master molecules will have to be degradable in order to produce a size reduction. This degradation step is then generally followed by a washing step. The smallest master molecules are generally removable by washing, the preliminary degradation step not being inevitably required. According to the present invention, a polymer is removable by washing when it can be removed for example, by a simple washing or soaking treatment in an aqueous solution, possibly acidified and/or heated or organic. Other removal techniques which lead to a degradation or not according to the polymers considered, which also form part of the invention, can also be used, alone or in combination, such as ultrasounds, chemical dissolution, extraction by a solvent, heating, mechanical effect, oxidations, depolymerization, supercritical liquid, microwave extraction, pyrolysis, extraction accelerated by solvent (ESA), enzymatic treatment and osmosis.

In all cases, it is of course necessary to make sure that the fingerprint itself is not affected by this removal step. For example, if oxidation is used, it is of course necessary that it is selective towards the master polymer, and does not damage the fingerprint matrix.

The master polymer can be of natural type.

In particular, it can be of biological origin. In this embodiment, we can for example mention the polypeptides, oligopeptides, proteins, polysaccharides, polynucleotides or polynucleosides.

The master polymer can also be synthetic. It can be obtained for example by step polymerization, such as polycondensation, chain polymerization such as anionic or cationic radicalar polymerization, or by ring opening or any other type of polymerization. In this embodiment, we can mention in a non-limitative way, the synthetic polymers or copolymers derived from at least one or more of the polymer families chosen from the polysaccharides, polyesters, polyamides, polyurethanes and polysiloxanes, optionally modified to comprise at least 5% of monomer units comprising at least one moiety of the target molecule(s).

The above-mentioned polymers have a degradable property in acceptable conditions to enable their removal from the molecular fingerprints being formed.

Amongst the non-degradable homopolymers or copolymers, we can mention those derived from at least one or more of the polymer families chosen from polyacrylates, polyacrylamides, polyvinylic, polyacroleine, polyacrylonitrile, poly (vinylic alcohol), polyalkylvinylketone, polybenzothiazole, polycarbonate of bisphenol A, poly (diallyldimethylammonium chloride), polyvinylchloride, polysiloxane, aromatic polyether, polyethersulfone, polyetherimide, polyethylenimine, polyimide, polyimidazole, polyoxymethylene, polyoxazole, polyoxyphenylene, polyoxytetramethylene, polyvinylalkylether, polyvinylpyrrolidone and polyvinylmethylketone. These homopolymers or copolymers will thus be removed by washing, as above-mentioned.

Either natural or synthetic, the master polymer can be an homopolymer or a copolymer which can notably be with blocks, graft, block, random, alternating, statistical, star-shaped, hyperbranched, dendrimer, comb-shaped or mixed copolymers, or even of polymer or copolymer type comprising directly on the main polymer chain, the grafts or side branches, at least one moiety of the target molecule(s). According to the present invention, "Capped master polymer" means the master polymer which comprises directly on the main polymer chain at least one moiety of the target molecule.

The master polymer can be cross-linked. In this case, it is advantageously degradable.

According to one preferred embodiment, the polymer contains at least 10% in number of monomer units being involved in the formation of the sites for identifying the target molecule(s).

According to another preferred embodiment, the polymer contains from 10 to 80% in number of monomer units being involved in the formation of the sites for identifying the target molecule(s), preferably from 15 to 60%, and even more preferably from 20 to 55%.

The use of this master polymer enables, amongst others, as was developed above, to stabilize the complex in balance between the master and the molecular fingerprint matrix in formation. Without binding the invention with the explanation which will follow, the inventors put forth the assumption that this stabilization would be possible thanks to an entropic gain, supporting the interactions of the polymer-polymer type in growth then polymer-polymer, and this compared to the approach consisting in using master molecules with a low mass, or in a more general way, with a mass close to the target molecules considered according to the invention. On the other hand, stabilization is increased by the integration of the target molecule to a polymeric chain. In fact, the movements of bonds within a polymeric chain are much more complex and slower than the Brownian movement of a small molecule. That results in much greater relaxation times. The connectivity of the chain implies that no bond can be moved independently from its neighbours. The moiety of target molecule as previously defined bound to a side chain of the master polymer, or being present on its main chain, will thus have a much more advantageous movement dynamic in order to stabilize a complex than an insulated master molecule, i.e. not bound to a polymeric structure.

Another advantage of the method for preparing molecular fingerprints according to the present invention is also in the fact that the master polymer can be designed according to the aimed applications, according to each target molecule.

Thereby, the method according to the present invention can be carried out with master polymers whose monomers are existing or can be synthesized according to the aimed target molecule. The target molecule or its moiety useful for the identification can thereby be integrated in a monomer for example thanks to a spacer, according to known methods of one skilled in the art, or even made polymerizable itself, always by techniques known by one skilled in the art.

Thereby, the bonds between the target molecule or its moiety useful for the identification, and the skeleton of the master polymer can be based on the formation of covalent bonds. Among these bonds, we can mention the amide or ester functions.

The molecule can further be bound to the monomer via a spacer. When using a spacer, the choice of the spacer depends on the functional groups present on the target molecule and the monomer of the master polymer. We can for example mention N-Succinimidyl 3-(2-pyridyldithio)propionate or N-(γ-maleimidobutyryloxy)succinimide ester which enables the connection between a molecule carrying an amine function and a molecule carrying a thiol. We can also mention the (4-N-maleimidophenyl) butyric hydrazide acid, which enables the connection between a molecule carrying an aldehyde function and a molecule having a thiol function.

The molecular fingerprints according to the present invention enable the identification capacity to be increased in comparison with the molecular fingerprints formed from master molecules identical to the target molecules, or from their analogues. Thereby, not only the density of sites for identifying can be increased, but the accessibility of said sites can also be improved.

Moreover, the master polymer can be easily recycled, which represents an important advantage of the present invention. Thereby, it is possible to recover the master polymers by a very simple precipitation technique, for example by heating if the polymer type allows it, or in a non-solvent, to obtain a product easily reusable, or by any other techniques of polymer purification or extraction such as fractionation, dialysis, etc. Indeed, on the contrary, when the master molecule is the target molecule or an analogue, the insulation is sometimes made difficult, even impossible after the fingerprint formation step.

According to a first alternative of the present invention, the master polymer is an homopolymer and the monomer units comprise the target molecule or its moiety useful for the identification in their structure. According to this alternative, the homopolymer is preferably linear, branched or star-shaped.

According to a particular embodiment of this alternative, the molecular fingerprint can be used to identify a target molecule corresponding to two, even three monomer units.

Typically, as is reported hereinafter and more particularly exemplified, the master polymer can be a polysaccharide and the fingerprint thereby formed, useful for the identification of a mono- or a disaccharide. Thereby, the use of dextrane as master polymer enables a molecular fingerprint to be obtained, ready to selectively retain glucose.

According to a second alternative of the present invention described hereinafter, and notably exemplified, the master polymer can be a copolymer. According to this second alternative, the master polymer is preferably of linear with blocks, alternating linear, branched, star-shaped or comb-shaped type.

Thereby, the use of a methylmethacrylate/BOC-(L)-O-méthacryloyle Tyrosine copolymer as master polymer enables a molecular fingerprint to be obtained, ready to retain in particular the BOC-(L)-Tyrosin and la BOC-(L)-Phenylalanine.

When the master polymer is a copolymer, the density of sites for identifying can be for example modulated while varying the ratio between the number of monomer units corresponding to the target molecule(s) and the total number of monomer units.

The use of a copolymer as master polymer can advantageously easily modify the properties of the master polymer. Thereby, we can for example provide monomer units promoting the solubilization of the master polymer in a given solvent. Consequently, we can also modify the solubility of the moiety forming the site for identifying. We can still vary its flexibility or its rigidity.

We can also design copolymers as master polymers in order to prepare multitarget fingerprints.

Using the implementation of this second alternative as an example, we can also mention the preparation of a naphthol identifying fingerprint from a styren/naphtyl acrylate master copolymer.

According to a particular embodiment of this second alternative, the master polymer can be a copolymer of the block –AAAAAAABBBBBCCCC or alternating ABCABCABCA or statistical AAABBCCBABAACCCABBB linear, branched, comb-shaped, star-shaped type, or of any other architecture type having a sufficiently large size so that it comprises at least three units of each A, B, C type. The target molecules to be identified are of A, B, C type or their analogue, or AB, AC, BC, ABC or other combinations of low mass, or their analogues.

The average total number of monomer units comprised in the homopolymer is preferably at least 6. Advantageously, the average number of monomer units comprised in the homopolymer or copolymer is comprised between 6 and 1,000, preferably between 10 and 100 for a non-degradable master polymer, and preferably between 10 and 500 for a degradable master polymer.

In order to illustrate the various structures likely to be adopted by the master polymer or copolymer used according to the present invention, we can particularly mention those where the whole or a part of the polymer or copolymer is:

in the form of graft copolymers, whose grafts comprise at least one moiety of the target molecule(s),
in the form of copolymers with blocks, for example di- or triblock, comprising linearly bound blocks, of which at least one of them comprises at least one monomer unit comprising at least one moiety of the target molecule(s),
in the form of a block, statistical, random copolymer or copolymer with gradient which comprises at least one monomer unit comprising at least one moiety of the target molecule(s),
in the form of a copolymer which comprises linearly bound blocks, and comprising at one or both of its ends, or even bound to the main polymeric chain, on the grafts or the side chains, at least one moiety of the target molecule(s),
in the form of a polymer which comprises at least one moiety of the target molecule(s) at one or both of its ends, or bound to the main polymeric chain, or
in the form of a mixed copolymer, comprising at least one moiety of the target molecules(s).

By "mixed copolymer", we mean a copolymer comprising polymeric chains of different type, namely block, statistical, random, alternating, with blocks, graft, star-shaped, capped or with gradient.

Of course, the present invention also covers the polymers and copolymers in which we combine several types of alternatives listed above and/or detailed hereinafter between them, either as it was described above for mixed copolymers, by the association of chains or blocks of more than two different types, or in the form of a mixture of different polymers or copolymers.

The master polymer or copolymer according to the present invention has a molecular mass in weight preferably comprised between 300 and 1,000,000, preferably between 500 and 100,000, and preferably between 1,000 and 20,000 for non-degradable polymers, and preferably between 1,000 and 100,000 for degradable master polymers.

With respect to the preparation of the copolymers according to the present invention, it can be carried out by any conventional polymerization technique. The method selection is generally carried out by taking the desired structure for the copolymer into account, namely for example graft copolymer or block copolymer and according to the reactivity and the preferential polymerization mode of the monomers involved. We can for example mention the radicalar, controlled, anionic, cationic polymerization. The polymerization can be implemented for example in solution, emulsion, suspension, by precipitation, in microemulsion or by polymerization in dispersed phase.

The master polymer can also, when it is cross-linked, take any form of structure. Thereby, the present invention further relates to a method according to the present invention, characterized in that the master polymer is cross-linked, branched, macroscopic array shaped or is a microgel.

The various master polymers listed hereinafter can be implemented according to the present invention:

low mass polysaccharides of dextrane type, for example having a mass of 1,000 to 10,000 or more, useful for the identification of glucose, or glucose dimer, such as a disaccharide,
glucose polyacrylate/polymethylmethacrylate copolymers, or of any other acrylate or methacrylate, useful for the identification of glucose,
any other polysaccharide or other oses, useful for the identification of glucose or glucose dimer, such as a disaccharide,
polystyrenes, having a mass of 600 to 20,000 for example, so as to preserve their removal capacity, useful for the identification of styren, toluene, benzene or any other analogue or dimer,
styren copolymers with any other monomer spacer of the styrenic groups such as methylmethacrylate, in order to limit the unfavorable steric effects, useful for the identification of styren, toluene, benzene or any other analogue or dimer,
styren sulphonate derivatives, useful for the identification of styren, toluene, benzene or any other analogue or dimer,
poly (bisphenol A co-epichlorohydrin), useful for the identification of bisphenol A,
poly (melamine-co-formaldehyde), useful for the identification of melamine,
DNA, useful for the identification of the bases,
polypeptides, useful for the peptide identification,
copolymers, of which one of the monomers is the naphtyl acrylate, useful for the identification of naphthol,
copolymers, of which one of the monomers is a derivative of an amino acid, useful for the identification of amino acids or analogues.
copolymers, of which one of the monomers is the BOC-(L)-O-methacryloyle Tyrosin, and the methylmethacrylate/BOC-(L)-O-methacryloyle Tyrosin copolymer for example, useful for the identification of the BOC-(L)-Tyrosin and BOC-(L)-Phenylalanine,
dextrane, useful for the identification of glucose,
agar, agarose and agaropectin, useful for the identification of $(1\rightarrow3)$-$\beta$-D-galactopyranose-$(1\rightarrow4)$-3,6-anhydro-$\alpha$-L-galactopyranose units,
alginate, useful for the identification of D-mannuronic acid and L-guluronic acid,
arabinoxylane, useful for the identification of $\alpha$-L-arabinofuranose et D-xylopyranose,
carrageenan, useful for the identification of D-galactopyranose,
carboxymethylcellulose (CMC), useful for the identification of carboxymethyl D-glucopyranose
cellulose and $\beta$-glucane, useful for the identification of D-glucopyranose,
gelatin, useful for the identification of polypeptide,
gellan gum, useful for the identification of linear tetrasaccharide $\rightarrow$4)-L-rhamnopyranosyl-($\beta$-1$\rightarrow$3)-D-glucopyranosyl-($\beta$-1$\rightarrow$4)-D-glucuronopyranosyl-($\beta$-1$\rightarrow$4)-D-glucopyranosyl-($\beta$-1$\rightarrow$ with O(2) L-glyceryl and O(6) acetyl substituents, or units taken separately,
guar gum, useful for the identification of D-mannopyranose or $\alpha$-D-galactose, pectin, useful for the identification of partially methyled D-galacturonic acid, α-(1→2)-L-rhamnosyl-α-(1→4)-D-galacturonosyle, L-arabinose and D-galactose units, starch, amylose and amylopectin, useful for the identification of D-glucose units, xanthan gum, useful for the identification of glucane D-glucopyranose, as well as the (3→1)-α-trisaccharide (3→1)-α-D-mannopyranose-bound-(2→1)-β-D-glucuronic acid-(4→1)-β-D-mannopyranose, chitosane, useful for the identification of N-acetyl-D-galactosamine and D-galactosamine, copolymers, of which one of the monomers is modified by a prostaglandin group, useful for the identification of the anti-ulceratives, copolymers, of which one of the monomers is modified by a barbiturate group, useful for the identification of the anti-epileptics, copolymers, of which one of the monomers is modified by a benzodiazepine group, useful for the identification of hypnotics, anxiolytics and myorelaxants, copolymers, of which one of the monomers is modified by a furosemide group, useful for the identification of diuretics, copolymers, of which one of the monomers is modified by a ranitidine and cimetidine group, useful for the identification of anti-ulceratives, copolymers, of which one of the monomers is modified by a sulfonamide group, useful for the identification of antibiotics, copolymers, of which one of the monomers is modified by a tetracycline group, useful for the identification of antibiotics, copolymers, of which one of the monomers is modified by a penicillin group, useful for the identification of antibiotics, copolymers, of which one of the monomers is modified by a chloramphenicol group, useful for the identification of antibiotics, copolymers, of which one of the monomers is modified by a macrolide group, useful for the identification of antibiotics, copolymers, of which one of the monomers is modified by a aminoside group, useful for the identification of antibiotics, copolymers, of which one of the monomers is modified by a quinolone group, useful for the identification of antibiotics, copolymers, of which one of the monomers is modified by a triazine or organophosphored group, useful for the identification of pesticides, copolymers, of which one of the monomers is modified by a group having organoleptic properties, useful for the identification of perfumes and flavours, copolymers, of which one of the monomers is modified by a riboflavine, carotenoid, tartrazine or amaranth group, useful for the identification of food colours, copolymers, of which one of the monomers is modified by a polyphenol or flavonoid group, useful for the identification of antioxidants, copolymers, of which one of the monomers is modified by an azo coloring, anthraquinoid, polymethinic, phthalocyanine group, useful for the identification of dyes, copolymers, of which one of the monomers is modified by a tocopherol, steroid or sterol group, useful for the identification of molecules having biological properties, copolymers, of which one of the monomers is modified by a toxic molecule or its analogue, useful for the identification of toxic molecules.

"Copolymers, of which one of the monomers is modified by" includes the copolymers for which the moiety useful for the identification is integrated in a monomer, for example thanks to a spacer, or is made polymerizable as above-mentioned.

The present invention further relates to the use of master molecules of polymeric type, called master polymers, removable by degradations and/or washing, for preparing molecular fingerprints comprising sites for identifying at least one target molecule, characterized in that at least 5% in number of the monomer units constituting said master molecules of polymeric type are involved in the formation of the sites for identifying the target molecule(s).

Method for Preparing, and Type of Fingerprint

The fingerprint polymerization step around the master polymer calls upon techniques known by one skilled in the art. We can thus refer to the article Peter A. G. Cormack et al, *Journal of Chromatography B*, 804 (2004) 173-182, which presents a review of the techniques available around the aspects of the molecular fingerprint polymerization. The contents of this article is given here as a reference.

The molecular fingerprint or more precisely the matrix constituting it, can thereby be formed by radicalar polymerization. The vinylic monomers, such as ethylene, styren and methylmethacrylate, are monomers which are particularly adapted for this technique. Any initiator can be used, such as azobisisobutyronitrile (AIBN).

The molecular fingerprint can also be formed by radicalar copolymerization, for varying the polymer properties. For example, we can mention methylmethacrylate/butylmethacrylate copolymer.

The molecular fingerprint can be made of cross-linked polymers or copolymers. According to the degree of crosslinking, we refer to branched polymer or copolymer, macroscopic lattices or microgels. Obtaining such polymers is possible thanks to the presence of crosslinking agents, which are multifunctional monomers. Divinylbenzene is a crosslinking agent which is used conventionally. The gel-type polymers are obtained in reduced presence of crosslinking agent, for example <5% or at higher degrees of crosslinking in the presence of small volumes of solvents. At higher degrees of crosslinking and/or in the presence of greater volumes of solvents, we can obtain macroporous polymers. Finally, when the volume of solvent used is increased beyond those normally used for the preparation of macroporous polymers, we can obtain microgels. These microgels are particularly interesting when we perform a polymerization by precipitation, advantageous to obtain spherical polymer particles of the micrometer size.

As monomers useful for the synthesis of the fingerprints, we can mention:
  acid monomers: acid monomers: methacrylic acid (MAA), p-vinylbenzoic acid, acrylic acid (AA), itaconic acid, 2-(trifluoromethyl)acrylic acid (TFMAA), acrylamido-(2-methyl)-propane sulfonic acid (AMPSA),
  basic monomers: 4-vinylpyridine (4-VP), 2-vinylpyridine (2-VP), 4-(5)-vinylimidazole, 1-vinylimidazole, allylamine, N,N'-diethylaminoethyl methacrylamide (DE-AEM), N-(2-aminethyl)-methacrylamide, N,N'-diethyl-4-styrylamidine, N,N,N-trimethylaminoethylmethacrylate, N-vinylpyrrolidone (NVP), ethylurocanic ester, neutral monomers: acrylamide, methacrylamide, 2-hydroxyethyl methacrylate (2-HEMA), trans-3-(3-pyridyl)-acrylic acid, acrylonitrile (AN), methyl methacrylate (MMA), styrene, ethylstyrene.

As crosslinking agents, we can mention: p-divinylbenzene (DVB), 1,3-diisopropenylbenzene (DIP), ethylenglykoldimethacrylate (EGDMA), tetramethylene dimethacrylate (TDMA), N,O-bisacryloyl-L-phenylalaminol, 2,6-bisacryloylamidopyridine, 1,4-phenylenediacrylamide, N,N'-1,3-phenylenebis(2-methyl-2-propenamide) (PDBMP), 3,5-bisacrylamidobenzoic acid, 1,4-diacryloylpiperazine (DAP), N,N'-methylenebisacrylamide (MDAA), N,N'-ethylenebismethacrylamide, N,N'-tetramethylenebismethacrylamide, N,N'-hexamethylenebismethacrylamide, anhydroerythritol dimethacrylate, 1,4;3,6-dianhydro-D-sorbitol-2,5-dimethacrylate, isopropoylenebis(1,4-phenylene) dimethacrylate, trimethylolpropane trimethacrylate (TRIM), pentaerythritol triacrylate (PETRA), pentaerythritol tetraacrylate (PETEA).

As initiator, we can mention: thermal initiators such as azobisisobutyronitrile (AIBN), azobisdimethylvaleronitrile (ABDV), benzyldimethylacetal and benzoylperoxide (BPO), 4,4'-azo(4-cyanovaleric) acid and the photochemical initiators such as the acetophenone derivatives, phosphine oxide derivatives, amino ketone derivatives, the binary systems of benzophenone and N-methyl diethanolamine type.

The solvents can not necessarily be foaming solvents, given the advantages already mentioned of the method for preparing according to the present invention. As commonly used foaming solvent, we can mention toluene and acetonitrile. A protic solvent such as water, alcohol or their mixture can also be used because of improved stabilization previously mentioned of the complex between the fingerprint and the master polymer.

It is also possible to modify the type of solvent so that the master polymer has a great conformation during the formation of the fingerprint, or a coiled conformation, using in this last case for example, a theta solvent.

It is further possible to directly modify the chemical type of master polymer to obtain the desired conformation in the forming medium of the fingerprint.

The methods for preparing molecular fingerprints according to the present invention, given the high density in sites for identifying being obtainable, have a considerable advantage compared to the traditional fingerprints when a method by precipitation is used for their preparation. Thereby, according to known techniques of the state of the art, it is necessary to increase the quantity of master molecules to increase the chances of creating molecular fingerprints in the microspheres obtained, because the solution is very diluted.

In the same way and for the same reasons, the molecular fingerprints according to the present invention are particularly advantageous in preparing microgels.

Thereby, thanks to the method according to the present invention, it is no longer necessary to use a great quantity of master polymer. In other words, the loss of a large quantity of master molecules, which was not used in the formation of the fingerprint, no longer has to be deplored, as is the case in the two prior arts above-mentioned: precipitation and formation method of the microgels.

Consequently, the present invention also covers the alternatives of methods for preparing according to the present invention, according to which the synthesis of the molecular fingerprint is done by polymerization in solution, emulsion, suspension, by precipitation, in microemulsion or by polymerization in dispersed phase, or is made in microgel preparation conditions.

A hybrid inorganic-organic method sol-gel can be used to manufacture the molecular fingerprint. In other words, the fingerprint matrix advantageously comprises an organosilicium-based lattice.

The silicon oxide solution can for example consist of a hybrid solution of organo-silicon (phenyltrimethoxysilane and methyltrimethoxysilane for example) and master polymer functionalized precursors.

We can refer to the two following articles to illustrate this alternative of the method for preparing the fingerprint according to the present invention: A. Olwill et al. "The Uses of Molecularly Imprinted sol-gels in Pharmaceutical Separations", *Biosensors and Bioelectronics* 20 (2004) 1045-1050, and R. Makote et al. "Template Recognition in Inorganic-organic Hybrid Films Pre-pared by the sol-gel Process", *Chem. mater,* 1998, 10, 2440-2445.

Applications

The molecular fingerprints according to the present invention are more particularly adapted to identify the target molecules of "small" size. Thereby, according to a preferred embodiment of the invention, the target molecules have a molecular weight lower than 300,000 g/mol, preferably 10,000 g/mol and even more preferably 1,000 g/mol.

The molecular fingerprints according to the present invention are particularly adapted to the trace analysis of one or more target molecules. Indeed, these molecular fingerprints, because master polymers are used, which are entities quite distinct from the target molecules, the effectiveness (of measurement in particular) of the fingerprints is not reduced when using by the salting-out of target molecules, as deplored when traditional fingerprints are used.

The fingerprints according to the present invention are also generally used in the extraction, separation, purification, detection, absorption, adsorption, retention and controlled release.

The fingerprints according to the invention are particularly used in agroalimentary, pharmacy, biomedical, food, defense or environment analyses.

They can also be used for sensors, such as biosensors, for molecular screening, directed chemical synthesis, sample treatment, combinatory chemistry, chiral separation, group shielding, catalysis, balance movement, polymer medicines and encapsulation.

The examples hereinafter are given by way of illustration, and without restricting the invention.

EXAMPLES

Example 1

Synthesis of a Molecular Fingerprint with Dextrane as Master Molecule for the Identification of Glucose 4 g of methylenebisacrylamide are dissolved at 60° C. in 8 ml of dimethylsulphoxide. A second solution is prepared by mixing 0.26 g of dextrane having an average molar mass of 90,000 and 0.46 g of acrylamide in 2 ml of dimethylsulphoxide at 50° C.

The two solutions are hot mixed. 91 mg of azobisisobutyronitrile are added, the solution is clear and transparent. The solution is degassed for 5 minutes by argon bubbling.

The polymerization is carried out over 48 hours at 50° C., and causes the formation of a white monolith.

A control sample is carried out as described above without dextrane. The polymer is a white monolith.

The monoliths are crushed then washed in an aqueous medium to remove the solvents and a part of the dextrane. The remainder of the dextrane is removed by several successive degradations in acidic medium at 60° C. To improve the washing, the samples are washed using a soxhlet in an aqueous medium. After screening, the particles having a size between 25 and 45 μm are used for the identification.

The percentage in number of the monomer units constituting the master polymer being involved in the formation of the sites for identifying glucose is 100%.

Example 2

Identification Property with Respect to Glucose in an Aqueous Medium 100 mg of each powder sample are placed in a pill organizer. After adding 1 ml of a glucose solution (1 mM, or 180 μg/mL), the pill organizers are stirred for two and a half hours, and the solutions are then analyzed by a glucose metering.

Glucose Metering Using the Glucose Oxidase Method:

The glucose is metered by a traditional method using glucose oxidase and peroxidase with o-dianisidine.

The glucose solution of the control samples and of the MIP is half diluted to be included in the measurable glucose content scale.

| Solution | Absorbance | Glucose content (μg/ml) |
|---|---|---|
| Standard 0 | 0.0153 | 0 |
| Standard 10 μg/ml | 0.1583 | 10 |
| Standard 25 μg/ml | 0.4096 | 25 |
| Standard 50 μg/ml | 0.7976 | 50 |
| Standard 90 μg/ml | 1.3333 | 90 |
| MIP | 1.1052 | 74 |
| Test | 1.2743 | 86 |

Therefore, the contents of the control samples and the MIP are 172 μg/mL and 148 μg/mL, respectively. These results are reproducible.

The control sample enables the nonspecific adsorption of glucose on the polymer to be measured. The metering shows a weak adsorption of glucose on the control sample since there were initially 180 μg of glucose in solution, and 172 μg remains.

The MIP cumulates the adsorption of glucose produced in a nonspecific way (similar to the control sample) and related to the identification by the matrix.

In the case of the MIP, 32 μg/mL of glucose have been adsorbed. 24 μg of glucose can thus be associated to the specific identification of glucose.

Example 3

Synthesis of the Styren Naphtholacrylate "PS-Naphthol" Master Copolymer Molecule, of a Naphthol Identifying Fingerprint from a Master Polymer According to the Invention, and of a Fingerprint from Naphthol as Master Molecule (Comparative)

In a balloon, 5.2 g of styren, 0.5 g of naphthylacrylate, 28.8 mg of azobisisobutyronitrile and 3.49 mg of dodecylthiol are mixed. The solution is supplemented to 20 ml with toluene. The solution is bubbled for 5 min with argon, and is placed at 70° C. for 15 hours. The (PS-Naphthol) polymer is recovered by precipitation in ethanol.

The divinylbenzene is washed several times by a basic solution saturated with KCl to remove the inhibitor. It is dried on $MgSO_4$. The azobisisobutyronitrile primer is recrystallized in acetone.

A mother solution containing 2.8 ml of methacrylic acid distilled beforehand, 32 ml of divinylbenzene and 44 ml of toluene is prepared. Several samples are prepared using 20 ml of the mother solution.

Control material: 20 ml of the mother solution to which 90 mg of AIBN are added.

PS-Naphthol fingerprint: 20 ml of the mother solution in which 2.15 g of PS-Naphthol described previously are dissolved, along with 90 mg of AIBN. This PS-Naphthol mass corresponds to an estimate of 2.24 mmol of naphthol.

The percentage in number of the monomer units constituting the master polymer being involved in the formation, in the PS-Naphthol fingerprint, of the sites for identifying naphthol is 12%. This percentage in number was determined by NMR of the $^1H$.

Naphthol fingerprint (comparative): 20 ml of the mother solution in which 0.392 g of naphthol (2.8 mmol) along with 90 mg of AIBN are dissolved.

The oxygen is driven out by bubbling the solutions for five minutes with argon.

The polymerization is carried out at 50° C. during 48 hours to form a white monolith. The polymers thereby formed are crushed, washed in a tetrahydrofuran solution for several hours, then by extraction with the soxhlet, and screened. The tetrahydrofuran solutions are then evaporated to concentrate them. By pouring them in ethanol, the solution used with the PS-naphthol sample shows a precipitation, that shows a recovery of a white polymer which constitutes a large part of master polymers used in the experiment (>70%).

The samples whose size is between 25 and 45 μm, are used for the study of the naphthol identification.

Example 4

Identifying Property with Respect to 1 mM Napthol 100 mg of each synthetized fingerprint in example 3 are placed in flasks with 1 ml of a 1 mM naphthol solution in acetonitrile. The solution is analyzed after 3 hours and 18 hours.

The adsorption is negligible on the control sample.

The table expresses the quantity of naphthol (in mg) adsorbed per gram of molecular fingerprint materials.

Table giving the mass of naphthol adsorbed (mg) per gram of molecular fingerprint materials.

| Fingerprint | 3 hours | 18 hours |
|---|---|---|
| PS-Naphthol | 0.288 | 0.360 |
| Naphthol (comparative) | 0.158 | 0.302 |

We observe an increase in the identification capacity respectively from 82% after 3 hours and 20% after 18 hours The two fingerprints adsorb naphthol and that shows a fingerprint effect. The adsorption on the PS-Naphthol fingerprint is much faster than on the Naphthol fingerprint, which seems to indicate a greater accessibility of the sites for identifying, and an increase in the density of sites for identifying.

Moreover, we note that the adsorption on the PS-Naphthol fingerprint is always significantly greater than for the Naphthol fingerprint.

Example 5

Comparison of the Identification Capacities of Naphthol to a Content of 100 mM 100 mg of each synthetized fingerprint in example 3 are placed in flasks with 1 ml of a 100 mM naphthol solution in acetonitrile. The solution is analyzed after 96 hours in order to reach the balance state. In fact, we use much greater naphthol content than in example 4, so as to determine the real identification capacity in over-content.

The adsorbed quantities are determined by HPLC by analyzing the contents of the supernatant solutions.

The table expresses the quantity of naphthol (in mg) adsorbed per gram of molecular fingerprint materials.

Table giving the mass of naphthol adsorbed (mg) per gram of molecular fingerprint materials.

| Fingerprint | 96 hours |
|---|---|
| PS-Naphthol | 13 |
| Naphthol (comparative) | 7.4 |

The two fingerprints adsorb the naphthol. The adsorption on the PS-Naphthol fingerprint is much greater. We observe an increase in the identification capacity by 74% compared to that of Naphthol fingerprint material.

Example 6

Synthesis of the Methylmethacrylate BOC-(L)-O-méthacryloyle Tyrosin Master Copolymer Molecule, of an Identifying Fingerprint of the BOC-(L)- Noted Phenylalanine "PMMA-BOC-(L)-Phenylalanine" from the Master Copolymer Molecule According to the Invention, and of a Fingerprint from the BOC-(L)- Phenylalanine as Master Molecule (Comparative)

In a balloon, 0.645 g of distillated methylmethacrylate, 0.968 g of the BOC-(L)-O-méthacryloyle Tyrosin, 5.3 mg of azobisisobutyronitrile and 0.321 g of dodecylthiol are mixed. The solution is supplemented with 4.5 ml of tetrahydrofuran. The solution is bubbled with nitrogen for 10 min, and is placed at 50° C. for 70 hours. 1.02 g of methylmethacrylate/ BOC-(L)-O-méthacryloyle Tyrosin master copolymer molecule are recovered by precipitation in cyclohexane. The number of monomer units determined by NMR on the polymethylmethacrylate (LDC) synthesized under these same conditions is about 15.

The dimethylacrylate of the ethyleneglykol is washed several times by a basic solution saturated with NaCl to remove the inhibitor. It is dried on MgSO$_4$. The azobisisobutyronitrile primer is recrystallized in acetone.

Three samples, each containing 295 mg of methacrylic acid distilled beforehand, 360 mg of 4-vinylpyridine, 6.12 g of the ethyleneglykol dimethylacrylate and 11 ml of acetonitrile are prepared.

To the first sample (control material), 286 mg of PMMA synthesized under the same conditions as the master copolymer molecule are added. The solution obtained is placed at 50° C. for one hour, then at 4° C. for 14 hours.

To the second sample (PMMA-BOC-(L)-Phenylalanine fingerprint), 500 mg of methylmethacrylate/BOC-(L)-O-méthacryloyle Tyrosin master copolymer molecule described previously are added. The solution obtained is placed at 50° C. during one hour then at 4° C. for 14 hours.

The percentage in number of the monomer units constituting the master polymer being involved in the formation, in the "PMMA-BOC-(L)-Phenylalanine" fingerprint, of the sites for identifying the BOC-(L)-Phenylalanine is 30%. This percentage in number was determined by NMR of the 1H.

To the third sample (comparative) (BOC-(L)-Phenylalanine fingerprint) 286 mg of PMMA synthesized under the same conditions as the master copolymer molecule, and 227 mg of BOC-(L)-Phenylalanine are added. The solution obtained is placed at 50° C. for one hour then at 4° C. for 14 hours.

In the three samples, the oxygen is driven out by bubbling the solutions for ten minutes with nitrogen, and 78 mg of azobisisobutyronitrile are added in each sample.

The polymerization is carried out at 50° C. for 56 hours to form a white monolith. The polymers thus formed are crushed, washed by a tetrahydrofuran solution for four hours, then by a tetrahydrofuran solution at 10% in acetic acid over night, and screened. The tetrahydrofuran solutions are then evaporated to concentrate them. By pouring them in cyclohexane, the solution used with the PMMA-BOC-(L)-Phenylalanine sample shows a precipitation which corresponds to a white polymer which constitutes a large part of the master copolymer molecule used in the experiment (>75%).

The particles whose size is between 25 and 45 μm, are introduced in a 150×4.6 mm HPLC column, and then pressure-packed and washed with acetonitrile to study the identification of the BOC-(L)-Tyrosin and of the BOC-(L)-Phenylalanine in HPLC.

Example 7

Identifying Property with Respect to BOC-(L)-Tyrosin and the BOC-(L)-Phenylalanine by HPLC 1 mM and 10 mM of BOC-(L)-Tyrosin in the acetonitrile, along with 10 mM of BOC-(L)-Phenylalanine are injected on the three columns filled with the "PMMA-BOC-(L)-Phenylalanine" fingerprint, the "BOC-(L)-Phenylalanine" fingerprint and the "control material", respectively.

The eluent used is an 0.1% acetonitrile solution of acetic acid, with a flow rate of 1 mL/min. The BOC-(1)-Tyrosin is detected at 277 nm, whereas the BOC-(1)-Phenylalanine is detected at 258 nm. Except for the 5 μL of ketone solution in acetonitrile used to determine the dead volume of the column, the injection volumes are 20 μL.

The retention times measured for each of the 3 columns as well as the mid-height widths of the peaks obtained are shown in the table below.

|  | Retention time (min.) BOC-(L)-Tyrosine | | Width of peak at half-height (min.) BOC-(L)-Tyrosine | | Retention time (min.) BOC-(L)-Phenylalanine | Width of peak at half-height (min.) BOC-(L)-Phenylalanine |
|---|---|---|---|---|---|---|
|  | 1 mM | 10 mM | 1 mM | 10 mM | 10 mM | 10 mM |
| Print PMMA-BOC(L)-Phenylalanine | 12.65 | 7.967 | 4.05 | 1.82 | 5.58 | 1.08 |
| Print BOC-(L) Phenylalanine | 15.20 | 9.00 | 6 | 3.16 | 7.87 | 2.20 |
| Test material | 6.367 | 5.167 | 1.67 | 1.38 | 2.85 | 0.77 |

All of the BOC-(L)-Tyrosin and of the BOC-(L)-Phenylalanine solutions present greater retention times for the two fingerprints than for the control material (polymer non-printed).

That illustrates the identification of said fingerprints with respect to the BOC-(L)-Tyrosin and the BOC-(L)-Phenylalanine.

The mid-height width of the peaks measured for the PMMA-BOC-(L)-Phenylalanine fingerprint according to the invention is also weaker than that measured for the BOC-(L)-Phenylalanine fingerprint, which indicates a greater homogeneity of the sites for identifying, as well as in their accessibility in the fingerprint prepared from PMMA-BOC-(L)-Phenylalanine master polymer according to the invention.

Example 8

Comparison of the Identification Capacities of the BOC-(L)-Tyrosin with a Content of 20 mM 100 mg of each of the two synthetized fingerprints in example 6 (PMMA-BOC-(L)-Phenylalanine fingerprint and BOC-(L)-Phenylalanine fingerprint are placed in flasks with 1 ml of a 20 mM solution of the BOC-(L)-Tyrosin in acetonitrile containing 0.1% of acetic acid. The solution is analyzed after 3 hours and 5 hours.

The adsorbed quantities are determined by HPLC by analyzing the contents of the supernatant solutions.

The table expresses the quantity of BOC-(L)-Tyrosin (in Mg) adsorbed per gram of molecular fingerprint materials.

Table giving the mass of BOC-(L)-Tyrosin adsorbed (in mg) per gram of molecular fingerprint materials.

| Fingerprint | 3 hours | 5 hours |
|---|---|---|
| PMMA-BOC-(L)-Phenylalanine | 12.1 | 12.0 |
| BOC-(L)-Phenylalanine (comparative) | 8.9 | 8.4 |

The two fingerprints adsorb the BOC-(L)-Tyrosin. The adsorption on the PMMA-BOC-(L)-Phenylalanine fingerprint is greater. We observe an 35% increase in the identification capacity compared to that of material with BOC-(L)-Phenylalanine fingerprint.

The invention claimed is:

1. A method for preparing a molecular fingerprint comprising sites for identifying at least one target molecule, the method comprising obtaining the fingerprint from at least one master molecule of polymeric type, called master polymer, by forming a matrix of the molecular fingerprint in the presence of the master polymer and removing said master polymer by degrading and/or washing the master polymer, wherein
said master polymer is different from the target molecule(s),
said master polymer is capable of being eliminated by degradation and/or washing,
at least 5% in number of monomer units constituting said master polymer are involved in the formation of the sites for identifying the target molecule(s), and the ratio between the molecular mass of the master polymer or the average molecular mass of all of the master polymers and the molecular mass of the target molecule or the average molecular mass of all of the target molecules is between 500 and 50,000.

2. The method according to claim 1, wherein the polymer contains from 10 to 80% in number of monomer units being involved in the formation of the sites for identifying the target molecule(s).

3. The method according to claim 2, wherein the polymer contains from 15 to 60% in number of monomer units being involved in the formation of the sites for identifying the target molecule(s).

4. The method according to claim 3, wherein the polymer contains from 20 to 55% in number of monomer units being involved in the formation of the sites for identifying the target molecule(s).

5. The method according to claim 1, wherein the monomer units being involved in the formation of the sites for identifying the target molecule(s) constitute together or separately at least one moiety of the target molecule(s).

6. The method according to claim 1, wherein at least 5% in number of monomer units constitute or comprise each at least one target molecule or one of its moieties useful for the identification.

7. The method according to claim 1, wherein at least two, three, even several monomer units, identical or different and subsequent reproduce together at least one target molecule, or one of its moieties useful for the identification.

8. The method according to claim 1, wherein the polymer is a homopolymer or a copolymer of a structure selected from the group consisting of blocks, grafted, block, random, alternating, statistical, star-shaped, hyperbranched, dendrimer, comb-shaped, and mixed; or of a structure wherein at least one moiety of the target molecule(s) is directly on a main polymer chain, grafts or side branches.

9. The method according to claim 8, wherein the homopolymer is linear, branched or star-shaped.

10. The method according to claim 8, wherein the copolymer is of linear with blocks, alternating linear, branched, star-shaped or comb-shaped type.

11. The method according to claim 9, wherein the average total number of monomer units in the copolymer is at least 6.

12. The method according to claim 10, wherein the average total number of monomer units in the copolymer is at least 6.

13. The method according to claim 8, wherein the average number of monomer units in the homopolymer or the copolymer is at least 6.

14. The method according to claim 8, wherein the average number of monomer units in the homopolymer or the copolymer is between 6 and 1000.

15. The method according to claim 8, wherein the average number of monomer units in the homopolymer or the copolymer is between 10 and 100 for a non-degradable master polymer.

16. The method according to claim 8, wherein the average number of monomer units in the homopolymer or the copolymer is between 10 and 500 for a degradable master polymer.

17. The method according to claim 1, wherein the master polymer is of biological origin.

18. The method according to claim 17, wherein the master polymer is selected from the group consisting of polypeptides, oligopeptides, proteins, polysaccharides, polynucleotides and polynucleosides.

19. The method according to claim 1, wherein the master polymer is obtained by step polymerization chain polymerization, or by ring opening.

20. The method according to claim 19, wherein the master polymer is a degradable polymer or copolymer derived from at least one or more of the polymer families selected from the group consisting of polysaccharides, polyesters, polyamides, polyurethanes and polysiloxanes.

21. The method according to claim 20, wherein said degradable polymer or copolymer is modified to comprise at least 5% of monomer units comprising at least one moiety of the target molecule(s).

22. The method according to claim 19, wherein the master polymer is a non-degradable polymer or copolymer derived from at least one or more of the polymer families selected from the group consisting of polyacrylates, polyacrylamides, polyvinylics, polyacrylein, polyacrylonitrile, poly(vinylic alcohol), polyalkylvinylketone, polybenzothiazole, polycarbonate of bisphenol A, poly(diallyldimethylammonium chloride), polyvinylchloride, polysiloxane, aromatic polyether, polyethersulfone, polyetherimide, polyethylenimine, polyimide, polyimidazole, polyoxymethylene, polyoxazole, polyoxyphenylene, polyoxytetramethylene, polyvinylalkylether, polyvinylpirrolidone and polyvinylmethylketone.

23. The method according to claim 1, wherein the master polymer is cross-linked, branched, macroscopic array shaped or is a microgel.

24. The method according to claim 1, wherein the synthesis of the molecular fingerprint is done by polymerization in solution, emulsion, suspension, by precipitation, in microemulsion or by polymerization in dispersed phase or is carried out in microgel preparation conditions.

* * * * *